United States Patent [19]

Sorochenko

[11] Patent Number: 4,637,390

[45] Date of Patent: Jan. 20, 1987

[54] ELECTROSURGICAL INSTRUMENT

[75] Inventor: Oleg A. Sorochenko, Kharkov, U.S.S.R.

[73] Assignee: Nauchno-Issledovatelsky Institut Obschei i Neotlozhno Khirurgii, Kharkov, U.S.S.R.

[21] Appl. No.: 769,987

[22] PCT Filed: Dec. 1, 1983

[86] PCT No.: PCT/SU83/00042

§ 371 Date: Jul. 30, 1985

§ 102(e) Date: Jul. 30, 1985

[87] PCT Pub. No.: WO85/02335

PCT Pub. Date: Jun. 6, 1985

[51] Int. Cl.[4] .............................................. A61B 17/36
[52] U.S. Cl. ........................... 128/303.14; 128/303.17
[58] Field of Search ........... 128/303.1, 303.14, 303.15, 128/303.16, 303.17, 317; 30/173, 265, 346.55, 346.56, 347, 355, 388; 83/846, 847, 848, 849, 850, 676

[56] References Cited

U.S. PATENT DOCUMENTS

| 336,739 | 2/1886 | Parker | 83/848 |
| 1,334,633 | 3/1920 | Pioche | 83/848 |
| 2,179,250 | 11/1939 | D'Amato | 128/317 |
| 4,257,301 | 3/1981 | Tuomaala | 83/676 |
| 4,436,009 | 3/1984 | Ask | 83/676 |

FOREIGN PATENT DOCUMENTS

| 2060397 | 5/1981 | United Kingdom . |
| 194982 | 6/1967 | U.S.S.R. . |
| 624617 | of 1978 | U.S.S.R. . |
| 639561 | 2/1979 | U.S.S.R. . |

OTHER PUBLICATIONS

S. Ja. Doletsky et al., High Frequency Electrosurgery, 1980, Meditsina Publ., Moscow, pp. 48–55.

Primary Examiner—Kyle L. Howell
Assistant Examiner—Randy Citrin
Attorney, Agent, or Firm—Fleit, Jacobson, Cohn & Price

[57] ABSTRACT

An electrosurgical instrument comprises a cutting portion which incorporates two active electrodes made as similar disk cutters (2, 3) arranged coaxially and at a clearance with respect to each other, a power actuator to impart rotation to the cutters (2, 3), and current leads to supply a diathermic current to the electrodes. The cutting edges of the disk cutters (2, 3) are essentially regularly alternating toothed portions (4, 5) and toothless portions, the toothed portions (4) of the cutter (2) being arranged staggerwise with respect to the toothless portions of the cutter (3).

2 Claims, 5 Drawing Figures

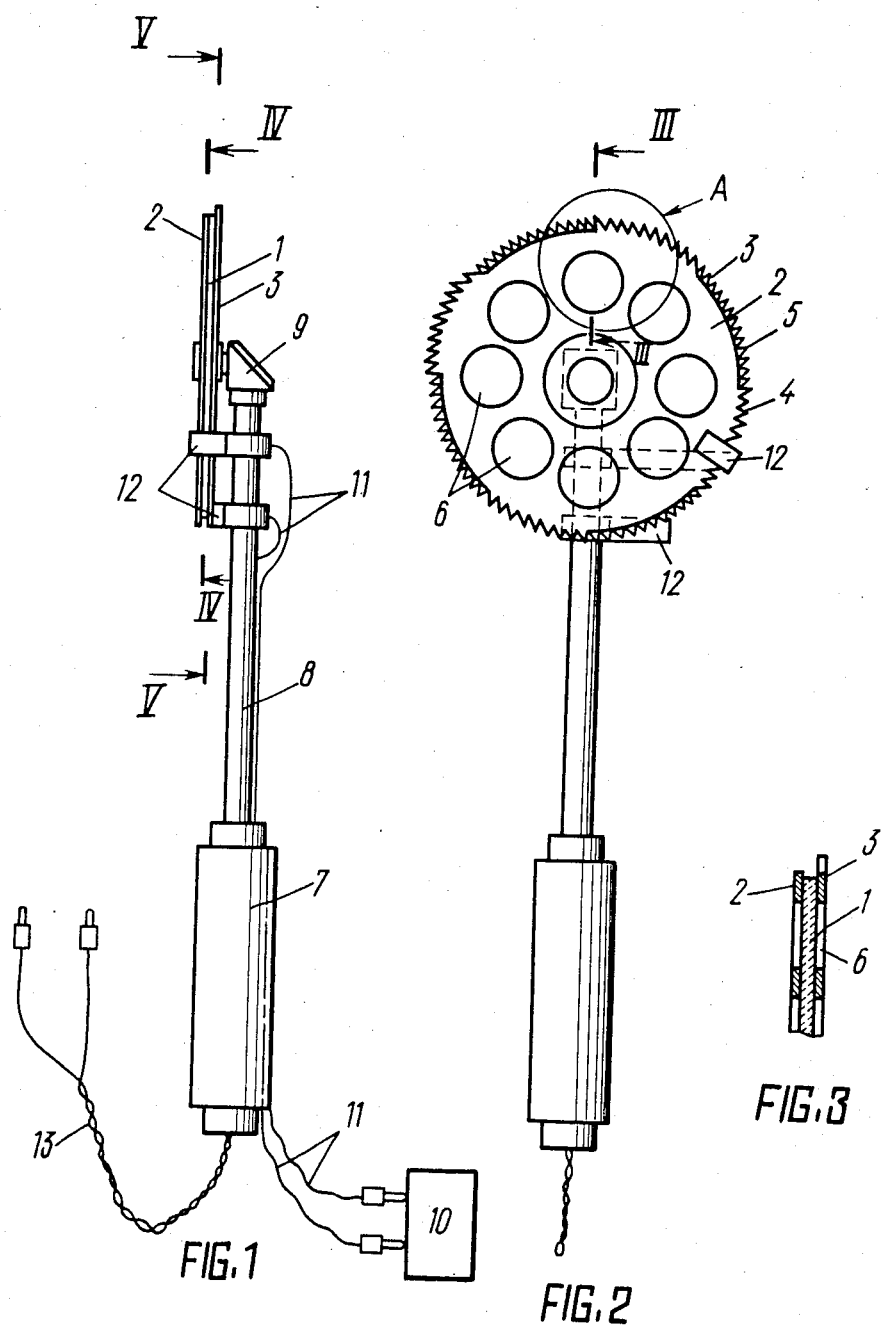

ELECTROSURGICAL INSTRUMENT

TECHNICAL FIELD

The present invention relates to surgery and more specifically it concerns electrosurgical instruments for bloodless surgical procedures.

BACKGROUND ART

Known in the art is an electrosurgical instrument for dissecting various tissues, comprising an active electrode, i.e., a double-edged disk knife to which a diathermic current is fed, and a passive electrode. The knife blade is provided with an adjoining scraper (cf. USSR Inventor's Certificate No. 624,617 published 1978).

During surgery the disk knife receives rotation and is fed with an electric current. The tissue operated upon is incised by virtue of motion performed by the instrument. The coagulate formed on the knife blade is removed by the scraper.

The aforedescribed instrument operates on the bipolar monoactive cutting principle, which involves a passive plate electrode connected to a patient's body a certain distance apart from the knife, i.e., an active electrode. It is due to r.f. current dispersion and useless heating of the tissues located between the active electrode and the passive one that surgery on the internal organs becomes uncontrolled and proceeds unstably. This is turn makes the instrument inapplicable for surgical interference on vitally important organs, e.g., for dissecting the sternum, the spine, the hipbone, and the like. Moreover, the device in question is unsuitable for surgery on the aforementioned osseocartilaginous tissues also due to the fact that these tissues features increased mechanical strength so that even a ground-sharp disk-shaped electrosurgical knife fails to destruct such tissues, since even an inconsiderable "biting" of the knife into the tissue results in its "jamming" therein.

Another electrosurgical instrument is known to comprise a cutting portion which incorporates an active electrode in the form of a disk cutter, and a power actuator to impart rotation to said cutter, a passive electrode, and current leads to feed a diathermic current to the active electrode (cf. USSR Inventor's Certificate No. 194,982 published 1967).

The instrument described above is suitable for surgery on hard osseocartilaginous tissues but cannot also be applied in the areas where vitally important organs are located, since this instrument, like the instrument described previously operates on the bipolar monoactive cutting principle.

DISCLOSURE OF THE INVENTION

The present invention has for its principal object to provide an electrosurgical instrument for surgery on hard osseocartilaginous tissues whose construction would preclude injury to vitally important organs in the course of surgery.

The object stated above is accomplished due to the fact that an electrosurgical instrument, comprising a cutting portion which incorporates an active electrode in the form of a disk cutter, and a power actuator for rotating said disk cutter, as well as current leads to supply a diathermic current to the instrument, according to the invention, is provided with an additional active electrode made as a disk cutter similar to the main disk cutter, and arranged coaxially and at a clearance with the main disk cutter, while the cutting edges of the disk cutters are in effect uniformly alternating toothed and toothless portions, and the toothed portions of one of the cutters are arranged staggerwise with respect to the toothless portions of the other disk cutter.

It is expedient that a number of holes be made in the disk cutters close to their cutting edges and be equispaced peripherally on said disk cutters.

An electrosurgical instrument provided in accordance with the present invention is for surgery on hard osseocartilaginous tissues, its application inflicting no injury upon the vitally important organs with r.f. currents since the instrument operates, according to the invention, on the principle of bipolar biactive electrosurgery to which is essential a local effect, that is, a possibility of an efficacious action on some tissue areas without danger to damage the adjacent ones.

BRIEF DESCRIPTION OF THE DRAWINGS

In what follows the present invention will now be disclosed in a detailed description of a specific illustrative embodiment thereof with reference to the accompanying drawings, wherein:

FIG. 1 is a general schematic view of an electrosurgical instrument;

FIG. 2 is a side view of an instrument of FIG. 1;

FIG. 3 is a sectional view of Area A in FIG. 1 taken along the line III—III;

BEST MODE OF CARRYING OUT THE INVENTION

Figure 4:
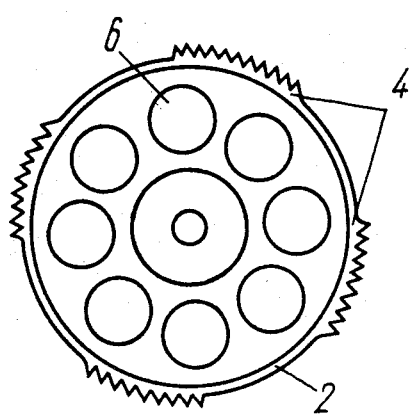
FIG. 4 is a sectional view of the instrument cutting portion taken along the line IV—IV in FIG. 1.
Figure 5:
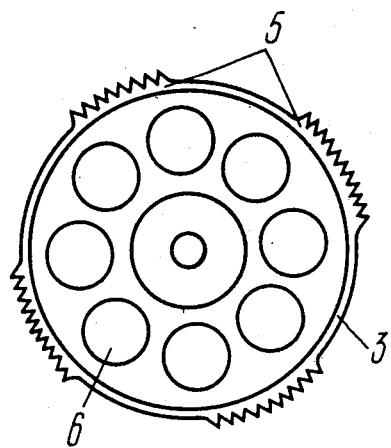
FIG. 5 is a sectional view of the instrument cutting portion taken along the line V—V in FIG. 1.

The electrosurgical instrument comprises a working cutting portion shaped as a disk 1 (FIGS. 1, 2, 3, 4, 5) which is made from an insulating material, each of the end faces of said disk carrying a disk cutter 2 and 3, respectively. The cutters 2 and 3 are similar to each other and are arranged coaxially and spaced some clearance apart, wherein the disk 1 is accommodated. The teeth of the cutters 2 and 3 are arranged discontinuously round the periphery of their cutting edges as separate portions 4, 5 and stand over the disk 1. In addition, the toothed portions 4, 5 alternate uniformly with the toothless portions. The toothed portions 4 of the cutter 2 are arranged staggerwise with respect to the toothed portions 5 of the cutter 3, that is, the cutters 2 and 3 are turned with respect to each other at an angle at which the toothed portion 4 (5) of one cutter 2 (3) does not overlap the toothed portion 5 (4) of the other cutter 3 (2). Holes 6 made in the disk cutters 2, 3 close to their cutting edges are equispaced peripherally on said cutters.

The disk 1 from an insulating material is connected to an electric motor 7 through an output shaft 8 and a gear speed reducer 9. The cutters 2, 3 are essentially active electrodes and are connected to a source 10 of a diathermic current through current leads 11 and movable contacts 12 made as springy knives each of which is adapted to contact the respective electrode, i.e., the disc current 2 or 3. The electric motor 7 is connected to a power source (omitted in the drawing) through a cord 13.

The instrument application techniques are as follows.

While carrying out surgery the electric motor 7 is switched on to impart rotation, via the gear speed reducer 9 and the output shaft 8, to the disk 1 and the cutters 2, 3. Simultaneously an r.f. current is applied, through the current leads 11 and the movable contacts 12, to the cutters 2, 3 which are in effect active electrodes. As a result, an r.f. electric field is created across the electrodes. Upon contacting the osseocartilaginous tissue by the teeth of the cutters 2, 3, said tissue is vigorously destructed, and the severed blood vessels are subjected to electrocoagulation.

It is due to an angular displacement of the toothed portions 4, 5 of the cutters 2, 3 that the clearance between the cutters 2 and 3 is not clogged with mechanically destructed tissue and coagulate. Coagulate that gets stuck to the outside surfaces of the cutters 2, is removed as fast as it is deposited, with movable contacts 12 shaped as springy blades.

Equidistant spacing of the toothed portions 4, 5 round the periphery of the cutters 2, 3 and their measuring alike simplify the manufacture and assembling of the instrument, as well as provide for mechanical cutting with a practically invariable thrust applied.

Provision of the holes 6 in the cutters 2, 3, located close to the cutting edges of the latter reduces the area of the electrodes in that portion of the instrument, whereby the current lines are concentrated predominantly on the cutting edges, thus adding to the efficacy of the electrocoagulation process.

INDUSTRIAL APPLICABILITY

The electrosurgical instrument, according to the invention, is for performing bloodless surgical interference on the osseocartilaginous tissues, and can find application in medicine and veterinary medicine.

I claim:
1. An electrosurgical instrument comprising:
   a first active electrode in the form of a disk cutter;
   a second active electrode identical to said first electrode disposed coaxially with said first electrode;
   a gap formed between said two electrodes;
   a disk of an insulating material having a diameter smaller than the diameters of said electrodes, said disk being located in said gap and being mounted coaxially with said electrodes;
   cutting edges of said disk cutters having toothed portions and toothless portions alternating regularly and having an identical length;
   said electrodes being so positioned relative to each other so that said toothed portions of one of said electrodes are disposed opposite said toothless portions of the other of said electrodes;
   current leads electrically connected to said electrodes for supplying diathermic current to said electrodes; and
   drive means for rotating said cutting edges around an axis passing through the centers of said electrodes.
2. An electrosurgical instrument as claimed in claim 1, wherein holes defined by said electrodes adjacent said cutting edges spaced uniformly along the circumference of said electrodes provide for concentrations of the lines of said diathermic current on said cutting edges.

* * * * *